(12) United States Patent
Marat et al.

(10) Patent No.: US 11,654,096 B2
(45) Date of Patent: May 23, 2023

(54) XYLOSIDE DERIVATIVES OF RESVERATROL FOR USE THEREOF IN COSMETICS

(71) Applicant: L'OREAL, Paris (FR)

(72) Inventors: Xavier Marat, Aulnay-sous-Bois (FR); Maria Dalko, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/955,616

(22) PCT Filed: Dec. 20, 2018

(86) PCT No.: PCT/EP2018/086219
§ 371 (c)(1),
(2) Date: Jun. 18, 2020

(87) PCT Pub. No.: WO2019/122140
PCT Pub. Date: Jun. 27, 2019

(65) Prior Publication Data
US 2021/0052479 A1 Feb. 25, 2021

(30) Foreign Application Priority Data
Dec. 21, 2017 (FR) ...................... 1762844

(51) Int. Cl.
*A61K 8/60* (2006.01)
*A61Q 19/08* (2006.01)
*C07H 15/203* (2006.01)

(52) U.S. Cl.
CPC .............. *A61K 8/602* (2013.01); *A61Q 19/08* (2013.01); *C07H 15/203* (2013.01)

(58) Field of Classification Search
CPC ............................. C07H 15/203; A61K 8/602
See application file for complete search history.

(56) References Cited

FOREIGN PATENT DOCUMENTS

| | | |
|---|---|---|
| EP | 1 175 888 A2 | 1/2002 |
| WO | WO 99/04747 A2 | 2/1999 |
| WO | WO199924009 * | 5/1999 |
| WO | WO 2010/067036 A1 | 6/2010 |

OTHER PUBLICATIONS

Dumas, Marc, English translation of WO99/24009, original patent published in 1999 (Year: 1999).*
Pruche, Francois et al., English translation of EP1175888, original patent published in 2002 (Year: 2002).*
Kylli, Petri et al., Journal of Agricultural and Food Chemistry, 2008, vol. 56, pp. 4797-4805 (Year: 2008).*
Hu et al., "Structural Modification of Stilbenoids from *Acanthopanax leucorrhizus* and Their Cytotoxic Activity", Chemistry and Biodiversity, vol. 14, No. 11 (Nov. 1, 2017), e1700244 (6 pages), XP055499706.
Kerem et al.: "Antioxidant Activity and Inhibition of α-Glucosidase by *trans*-Resveratrol, Piceid, and a Novel *trans*-Stilbene from the Roots of Israeli *Rumex bucephalophorus* L.", J. Agricultural and Food Chemistry, vol. 54, Jan. 20, 2006, pp. 1243-1247, XP002783827.

* cited by examiner

*Primary Examiner* — Bahar Craigo
(74) *Attorney, Agent, or Firm* — Polsinelli PC

(57) ABSTRACT

The present invention relates to the use of a compound of formula (I): in which R1, R2 and R3 independently denote: —a group of formula (II), or —a hydrogen atom H, it being understood that at least one of the radicals R1, R2, R3 denotes a group of formula (II); and also the salts thereof, the solvates thereof, and/or the isomers thereof, for preventing and/or cosmetically treating the signs of skin aging.

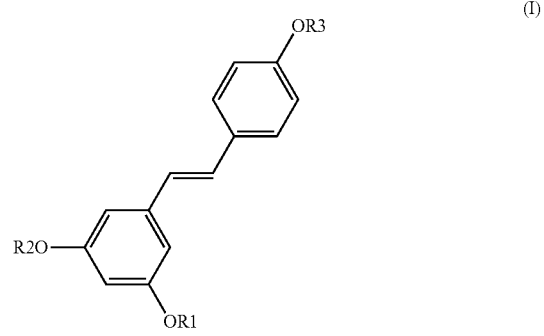

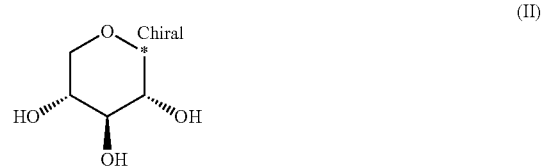

9 Claims, No Drawings

XYLOSIDE DERIVATIVES OF RESVERATROL FOR USE THEREOF IN COSMETICS

CROSS REFERENCE TO RELATED APPLICATIONS

This application is a National Phase filing under 35 U.S.C. § 371 of PCT/EP2018/086219 filed on 20 Dec. 2018; which application in turn claims priority to Application No. 1762844 filed in France on 21 Dec. 2017. The entire contents of each application are hereby incorporated by reference.

The present invention relates to the non-therapeutic cosmetic use of xyloside derivatives of resveratrol, and to the compositions, in particular cosmetic compositions, comprising them, for combating the aging of keratin materials, in particular skin aging.

Women and men currently have a tendency to wish to appear youthful for as long as possible and consequently seek to tone down the signs of aging of keratin materials such as skin aging, which are reflected in particular by wrinkles and fine lines. In this regard, the advertising and fashion industries mention products for retaining radiant and wrinkle-free skin, signs of youthful skin, for as long as possible, all the more so since physical appearance has an effect on the psyche and/or on morale.

Hitherto, wrinkles and fine lines were treated using cosmetic products containing active agents acting on the skin, for example by improving its cell renewal or alternatively by promoting the synthesis, or preventing the degradation, of the elastic fibers which make up skin tissue.

It is known that human skin is constituted of two tissues, a surface tissue, the epidermis, and a deep tissue, the dermis.

Natural human epidermis is composed mainly of three types of cells, namely keratinocytes, which form the vast majority, melanocytes and Langerhans cells.

The dermis provides the epidermis with a solid support. It is also its nourishing element. It is constituted mainly of fibroblasts and an extracellular matrix composed predominantly of collagen, elastin and a substance known as ground substance. These components are synthesized by the fibroblasts. Leukocytes, mast cells or else tissue macrophages are also found therein. Finally, blood vessels and nerve fibers pass through the dermis.

The dermal extracellular matrix is composed of proteins belonging to several large families: collagens, matrix glycoproteins other than collagens (fibronectin, laminin), elastin and proteoglycans. Glycosaminoglycans in free form (i.e. not bound to a protein) are also found in the extracellular matrix of the dermis.

It is now well established that specific interactions exist between these various classes of proteins so as to give rise to a functional tissue.

An extracellular space (micromatrix) also exists in the epidermis. This space plays an extremely important functional role in cell tissue renewal and/or maintenance.

Proteoglycans are complex macromolecules constituted of a branched central protein core, or network of proteins, to which very large numbers of polysaccharide side chains, called glycosaminoglycans, are attached.

In the remainder of the present application, proteoglycans will be denoted by the abbreviation PGs and glycosaminoglycans by the abbreviation GAGs.

GAGs have long been referred to by the expression "acid mucopolysaccharides" due to their high water retention capacity, their glucidic nature and their acid character originating from their multiple negative charges.

Thus, the polarity of GAGs makes them implicitly participate in certain biological functions such as tissue hydration, cation binding or an ionic filtration barrier role.

PGs and GAGs are synthesized by various cells in the dermis and epidermis: fibroblasts, keratinocytes and melanocytes.

Fibroblasts synthesize predominantly collagens, matrix glycoproteins other than collagens (fibronectin, laminin), GAGs, proteoglycans and elastin. Keratinocytes predominantly synthesize sulfate-containing GAGs and hyaluronic acid whereas melanocytes produce ostensibly no hyaluronic acid.

At the time of their incorporation into a PG, GAGs are in the form of linear chains composed of repeats of a base disaccharide always containing a hexosamine (glucosamine or galactosamine) and another monosaccharide (glucuronic acid, iduronic acid or galactose). The glucosamine is either N-sulfated or N-acetylated. On the other hand, the galactosamine is always N-acetylated. In addition, there may be sulfate groups O-linked to the hexosamine, uronic acid and galactose.

The strong anionic nature of GAGs is explained by the presence of carboxylate groups within the hexuronic acids (glucuronic acid and iduronic acid) and of O- and N-linked sulfate groups.

The main GAGs are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS), which differs from the other glycosaminoglycans by the presence of galactose in place of uronic acid.

GAGs may also exist in the extracellular matrix in free form, that is to say not bound to a matrix protein: this is especially the case for hyaluronic acid.

When PGs are synthesized, the GAGs are polymerized from these anchoring structures.

The synthesis of GAGs requires the coordinated and concerted action of very specific enzymes (transferases, epimerases, sulfotransferases) which are adjacent in the membrane of the endoplasmic reticulum and of the Golgi apparatus. A multitude of biochemical reactions (N-deacetylation, N- and O-sulfations, epimerization) then modify the two constituent monosaccharides of the base unit in a nonuniform manner along the chain. From one heparan sulfate chain to another, for example, the glucuronic acid/iduronic acid ratio, the nature, the number and the position of the O-sulfations, and also the N-sulfate/O-sulfate ratio can vary, which potentially offers an immense structural diversity.

Generally, the biological roles of PGs are highly diversified, ranging from a passive mechanical support function (for example serglycins) or from an ion barrier role in molecular filtration (for example perlecan and bamacan of the glomerular basement membrane), to more specific effects in cell adhesion, cell spreading, cell proliferation, cell differentiation or morphogenesis, or to very specific effects of PG-protein interactions, such as betaglycan receptor function or the interaction of decorin with collagen. They also play a fundamental role in the controlled release of various growth factors.

One of the roles of dermal connective tissue is to protect the body against external attacks while simultaneously forming an informative interface.

To do this, the dermis has high mechanical strength while maintaining, however, great flexibility.

Its strength is provided by the dense network of collagen fibers, but it is the PGs and the hyaluronic acid which, by providing the moisturization, distribution and flexibility of the fibers, make the difference between the skin and, for example, leather.

PGs make up 0.5 to 2% of the dry weight of the dermis, collagen, by itself, representing up to 80% thereof.

The concentration and distribution of GAGs and PGs in human skin vary with age. Hyaluronic acid or hyaluronan (HA) is the main GAG of the dermis, the latter containing half the HA of the body.

The synthesis of HA is performed in particular by the fibroblasts, close to the inner face of the plasma membrane. It is performed continuously. This gigantic polysaccharide (several million daltons) has a very high intrinsic viscosity, ensuring the moisturization and assembly of the various components of the connective tissue by forming supramolecular complexes.

Dermatan sulfate (DS), which was first isolated from the dermis, is also very abundant in the skin. It constitutes 40% to 50% of the dermal GAGs.

At the same time as the mechanisms contributing to the production of these specialized extracellular matrices, continual remodeling processes exist, the regulation of which depends on the balance between synthesis and degradation of the protein elements of the matrix.

Several families of matrix proteases are now described, and also the factors involved in the activation-inactivation thereof.

During chronological and/or photoinduced aging, the dermis and the epidermis undergo numerous modifications and degradations which are reflected, with age, by flaccidness and a loss of suppleness of the skin.

Among the components degraded (in particular collagen and elastin), the PGs and GAGs are also adversely affected. Specifically, over the course of aging, the fibroblasts and keratinocytes produce fewer and fewer PGs and GAGs and the synthesis thereof is imperfect. This results in significant disorganization: the deposition of GAGs on the protein backbone forming the PG is abnormal, which results in a lower avidity of these PGs for water and therefore a reduction in the hydration and tonicity of the tissues. Restoring a normal production of PGs and GAGs by fibroblasts and keratinocytes contributes partially towards compensating for the loss of moisturization of the skin.

The degradation of these matrices thus contributes to the phenomenon of dryness and loss of suppleness of the skin.

The importance of being able to have available products of which the effects are directed toward maintaining the level of PGs and GAGs in the skin and thus of maintaining, inter alia, good moisturization and good suppleness of the skin, can thus be appreciated.

The synthesis of resveratrol glycosides, and in particular the compounds CAS: 195989-55-0 and CAS: 1245637-91-5, is known from document Zhongguo Yaowu Huaxue Zazhi (2010), 20(1), 19-24.

The use of certain glucosylated derivatives of resveratrol for combating the signs of skin aging is known from patent EP 1 175 888.

The applicant has discovered, surprisingly and unexpectedly, that xyloside derivatives of resveratrol are capable of improving the synthesis of sulfated glycosaminoglycans such as chondroitin sulfate and dermatan sulfate.

Their efficiency is greater than that of the resveratrol and polydatin (resveratrol glucoside) compounds that are already known. They are more effective for improving epidermal renewal and firmness of the skin and for more effectively combating the signs of skin aging. They also have a beneficial effect on the structure of the dermal-epidermal junction, in particular on the cohesion between dermis and epidermis.

These novel compounds therefore find a particular application in compositions, in particular cosmetic compositions, intended for preventing and/or cosmetically treating skin aging; especially preventing and/or treating, in particular topically, the signs of skin aging, and most particularly the signs on the skin related to wrinkled skin, skin exhibiting a detrimental modification of its viscoelastic or biomechanical properties, skin exhibiting a detrimental modification of the cohesion of its tissues, thinned skin and/or skin exhibiting a detrimental modification of its surface appearance.

The present invention thus relates to the non-therapeutic cosmetic use of compounds of formula (I) as defined hereinafter, for preventing, reducing and/or treating the signs of the aging of keratin materials, in particular the signs of skin aging.

The compounds according to the invention can make it possible more particularly to maintain and/or restore the mechanical properties of keratin materials impaired by the aging process, such as the extensibility, tonicity, firmness, suppleness, density and/or elasticity properties of the skin.

The term "biomechanical or mechanical properties" is intended to mean herein more particularly the extensibility, tonicity, firmness, suppleness and/or elasticity properties of keratin materials, in particular of the skin.

The term "signs of skin aging" is intended to mean herein any modification of the outer appearance of the skin due to aging, whether it is chronobiological and/or extrinsic aging, in particular photoinduced or hormonal aging; among these signs, it is possible to distinguish:

wrinkled skin, which is reflected in particular by the appearance of wrinkles and/or fine lines;

skin exhibiting a detrimental modification of its viscoelastic or biomechanical properties, or skin exhibiting a lack of elasticity and/or of stretchability and/or of firmness and/or of suppleness and/or of tonicity, which is reflected in particular by wizened, flaccid, slack or saggy skin;

skin exhibiting a detrimental modification of the cohesion of its tissues;

thinned skin;

skin exhibiting a detrimental modification of its surface appearance, which is in particular reflected by a detrimental modification of the grain of the skin, for example roughness.

For the purposes of the present invention, the term "keratin materials" is intended to mean human keratin materials, and in particular the skin, bodily hair, the eyelashes, head hair, the lips and the nails of human beings.

The term "skin" is intended to mean all of the skin of the body, including the scalp, the mucous membranes and the semi-mucous membranes. More particularly, in the present invention, the skin of the neckline, the neck and the face, the hands, the underarms and especially the skin of the face, are considered.

More particularly, for the purposes of the present invention, the keratin materials denote human skin.

A subject matter of the present invention is thus the non-therapeutic cosmetic use of at least one compound of formula (I):

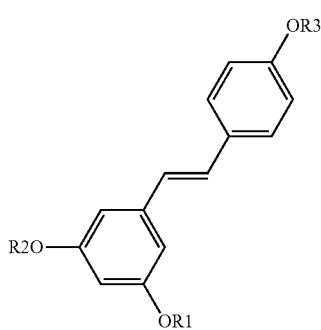

(I)

in which R1, R2 and R3 independently denote:
a group of formula (II), or

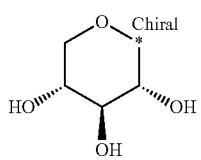

(II)

a hydrogen atom H,
it being understood that at least one of the radicals R1, R2, R3 denotes a group of formula (II);
and also the salts thereof, the solvates thereof, and/or the isomers thereof, for preventing and cosmetically treating the signs of the aging of keratin materials, in particular the signs of skin aging.

The asterisk "*" denotes the point of attachment of the radical to the rest of the compound.

The invention thus extends to the isomers of the compounds of formula (I), alone or as a mixture in any proportions, and also to the physiologically acceptable salts and/or the solvates of these compounds.

For the purposes of the present invention, the term "isomers" is intended to mean the optical isomers and/or the geometric isomers, it being understood that the stereochemistry of the hydroxyl groups is fixed and as represented in formula (II).

The compounds of formula (I) in accordance with the invention can be used alone or as a mixture and in any proportion.

The anomeric-C bond(s) in formulae (I) may be α or β anomeric.

According to one particular form of the invention, the anomeric-C bond(s) in formulae (I) are β anomeric.

According to another particular form of the invention, the anomeric-C bond(s) in formulae are α anomeric.

For the purposes of the present invention, the term "mixture" relates to the mixtures of the various isomeric forms of one and the same compound, and likewise the mixtures of various compounds of general formula (I) and/or the respective isomeric forms thereof.

According to the present invention, the isomers of the compounds of formula (I) are chosen from the enantiomers, the Z- and E-form isomers, the α or β anomers, and mixtures thereof.

According to a particular form of the invention, the compounds of formula (I) are E isomers.

In the context of the present invention, the salts of the compounds of formula (I) comprise the conventional non-toxic salts of said compounds such as those formed from a base.

As salts of the compound of formula (I), mention may be made of the salts obtained by addition of the compound of formula (I) with a base, which may be organic or mineral. The base may thus be a mineral base, such as sodium hydroxide, potassium hydroxide, calcium hydroxide, ammonium hydroxide, magnesium hydroxide, lithium hydroxide, or sodium, potassium or calcium carbonate or hydrogen carbonate, for example. The base may also be an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made especially of 2-amino-2-methylpropanol, ethanolamine, triethanolamine, 2-dimethylaminopropanol, 2-amino-2-(hydroxymethyl)-1,3-propanediol and 3-(dimethylamino)propylamine. The salts may also denote salts of addition with amino acids, for instance lysine, arginine or guanidine.

Advantageously, the salts of the compounds of formula (I) may be chosen from alkali metal or alkaline-earth metal salts such as sodium, potassium, calcium or magnesium salts; ammonium salts.

The solvates comprise conventional solvates such as those formed during the preparation of said compounds due to the presence of solvents. Examples that may be mentioned include solvates due to the presence of water or of linear or branched alcohols, such as ethanol or isopropanol.

According to one particular embodiment of the invention, the compounds of formula (I) and also the salts thereof, the solvates thereof and/or the isomers thereof are such that one and just one of the radicals R1 or R2 or R3 denotes a group of formula (II) and preferably R1 or R3 denotes a group of formula (II).

In one particular embodiment, the invention relates to the non-therapeutic use, for preventing and/or cosmetically treating the signs of the aging of keratin materials, in particular the signs of skin aging, of at least one compound of formula (I) and preferably a compound of formula (I) and also the salts thereof, the solvates thereof and/or the isomers thereof, in which:
R1 denotes a group of formula (II)

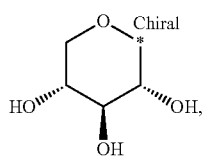

(II)

and
R2 and R3 each denote a hydrogen atom H.

In another particular embodiment, the invention relates to the non-therapeutic use, for preventing and/or cosmetically treating the signs of the aging of keratin materials, and in particular the signs of skin aging, of at least one compound of formula (I) and preferably a compound of formula (I) and also the salts thereof, the solvates thereof and/or the isomers thereof, in which:

R2 denotes a group of formula (II)

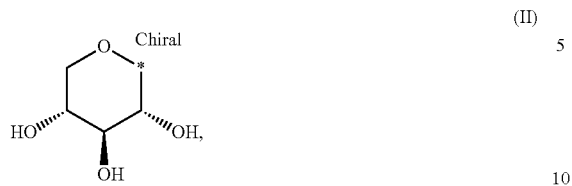
(II)

and

R1 and R3 each denote a hydrogen atom H.

Preferably, the compounds of formula (I) are chosen from the following compounds:

| Compound | Structure | Chemical name |
|---|---|---|
| 1 | 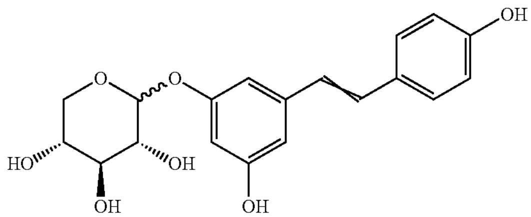 [SMILES: Oc1ccc(C=Cc2cc(O)cc(OC3OC[C@@H](O)[C@H](O)[C@H]3O)c2)cc1] | 3-hydroxy-5-[2-(4-hydroxy-phenyl)ethenyl]phenyl xylopyranoside |
| 2 | | 4-[2-(3,5-dihydroxy-phenyl)ethenyl]phenyl xylopyranoside | and also the salts thereof, the solvates thereof and/or the isomers thereof.

In particular, the compounds of formula (I) are chosen from the compounds 1a, 2a, 1b and 2b below, and also the salts thereof, and/or the solvates thereof:

| Compound | Structure | Chemical name |
|---|---|---|
| 1a | 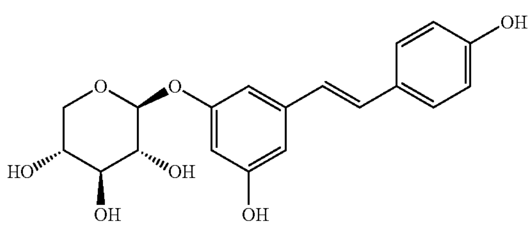 [SMILES: Oc1ccc(/C=C/c2cc(O)cc(O[C@@H]3OC[C@@H](O)[C@H](O)[C@H]3O)c2)cc1] | 3-hydroxy-5-[(E)-2-(4-hydroxyphenyl)ethenyl]phenyl β-D-xylopyranoside |
| 2a | 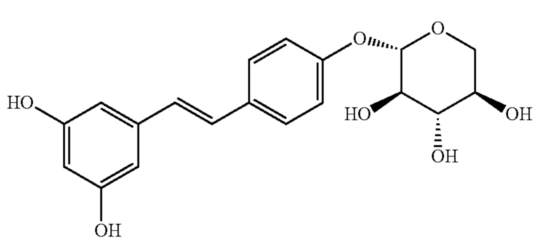 [SMILES: Oc1cc(O)cc(/C=C/c2ccc(O[C@@H]3OC[C@@H](O)[C@H](O)[C@H]3O)cc2)c1] | 4-[(E)-2-(3,5-dihydroxy-phenyl)ethenyl]phenyl β-D-xylopyranoside |

| Compound | Structure | Chemical name |
|---|---|---|
| 1b | 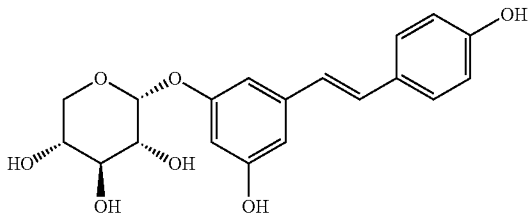 [SMILES: Oc1ccc(/C=C/c2cc(O)cc(O[C@H]3OC[C@@H](O)[C@H](O)[C@H]3O)c2)cc1] | 3-hydroxy-5-[(E)-2-(4-hydroxyphenyl)ethenyl]phenyl α-D-xylopyranoside |
| 2b | 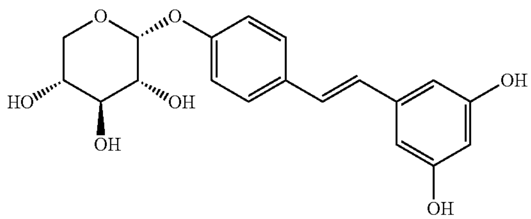 [SMILES: Oc1cc(O)cc(/C=C/c2ccc(O[C@H]3OC[C@@H](O)[C@H](O)[C@H]3O)cc2)c1] | 4-[(E)-2-(3,5-dihydroxyphenyl)ethenyl]phenyl α-D-xylopyranoside |

More particularly, the compounds of formula (I) are chosen from the compounds 1a and 2a below, and also the salts thereof, and/or the solvates thereof:

| Compound | Structure | Chemical name |
|---|---|---|
| 1a | 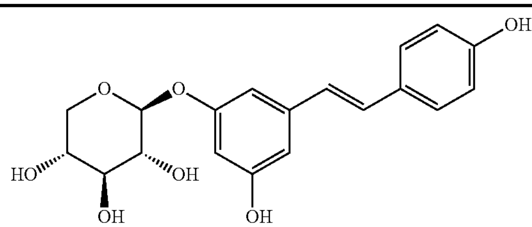 | 3-hydroxy-5-[(E)-2-(4-hydroxyphenyl)ethenyl]phenyl β-D-xylopyranoside |
| 2a | 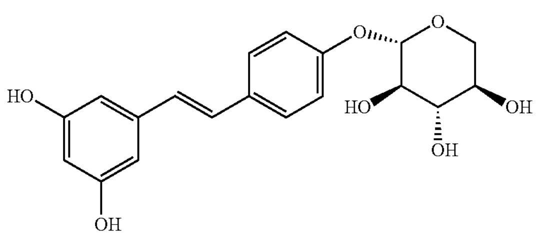 [SMILES: Oc1cc(O)cc(/C=C/c2ccc(O[C@@H]3OC[C@@H](O)[C@H](O)[C@H]3O)cc2)c1] | 4-[(E)-2-(3,5-dihydroxyphenyl)ethenyl]phenyl β-D-xylopyranoside |

According to one preferred form of the invention, the invention relates to the non-therapeutic use, for preventing and/or cosmetically treating the signs of the aging of keratin materials and in particular the signs of skin aging, of the compound of formula 1 and also the salts thereof, the solvates thereof and/or the isomers thereof (Z and/or E isomers and α or β anomeric-C bonds).

| Compound | Structure | Chemical name |
|---|---|---|
| 1 | 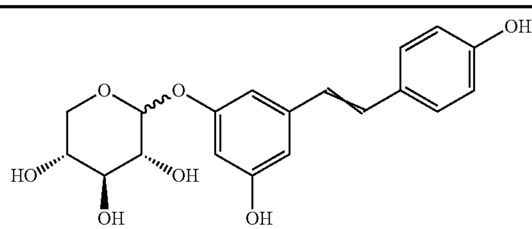 | 3-hydroxy-5-[2-(4-hydroxyphenyl)ethenyl]phenyl xylopyranoside |

According to this form of the invention, the compound of formula (I) denotes the compound 1a and also the salts thereof and/or the solvates thereof.

| Compound | Structure | Chemical name |
|---|---|---|
| 1a | 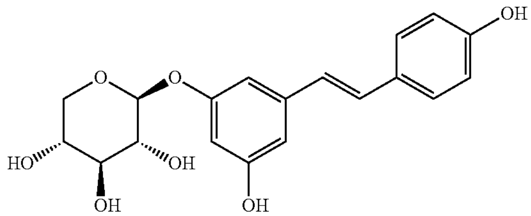 [SMILES: Oc1ccc(/C=C/c2cc(O)cc(O[C@@H]3OC[C@@H](O)[C@H](O)[C@H]3O)c2)cc1] | 3-hydroxy-5-[(E)-2-(4-hydroxyphenyl)ethenyl]phenyl β-D-xylopyranoside |

More particularly, the present invention relates to the non-therapeutic use of at least one compound of formula (I) and preferably a compound of formula (I) as previously described, said compound of formula (I) preferably being chosen from the compounds 1 and 2 and in particular chosen from the compounds 1a, 2a 1b and 2b, and more particularly chosen from the compounds 1a and 2a and also the salts thereof, the solvates thereof, and/or the isomers thereof, for preventing and/or cosmetically treating the signs of the aging of keratin materials, in particular the signs of skin aging, chosen from wrinkled skin, skin exhibiting a detrimental modification of its viscoelastic or biomechanical properties, skin exhibiting a detrimental modification of the cohesion of its tissues, thinned skin and skin exhibiting a detrimental modification of its surface appearance The invention also relates to the non-therapeutic cosmetic use of at least one compound of formula (I) and in particular a compound of formula (I) as previously described, preferably of at least one compound chosen from the compounds 1 and 2 and in particular chosen from the compounds 1a, 2a 1b and 2b, and more particularly chosen from the compounds 1a and 2a and also the salts thereof, the solvates thereof, and/or the isomers thereof, for improving the firmness of the skin and/or for improving the structure of the dermal-epidermal junction and/or for reinforcing the cohesion between the dermis and the epidermis.

The compounds of formula (I) can be prepared according to scheme I below:

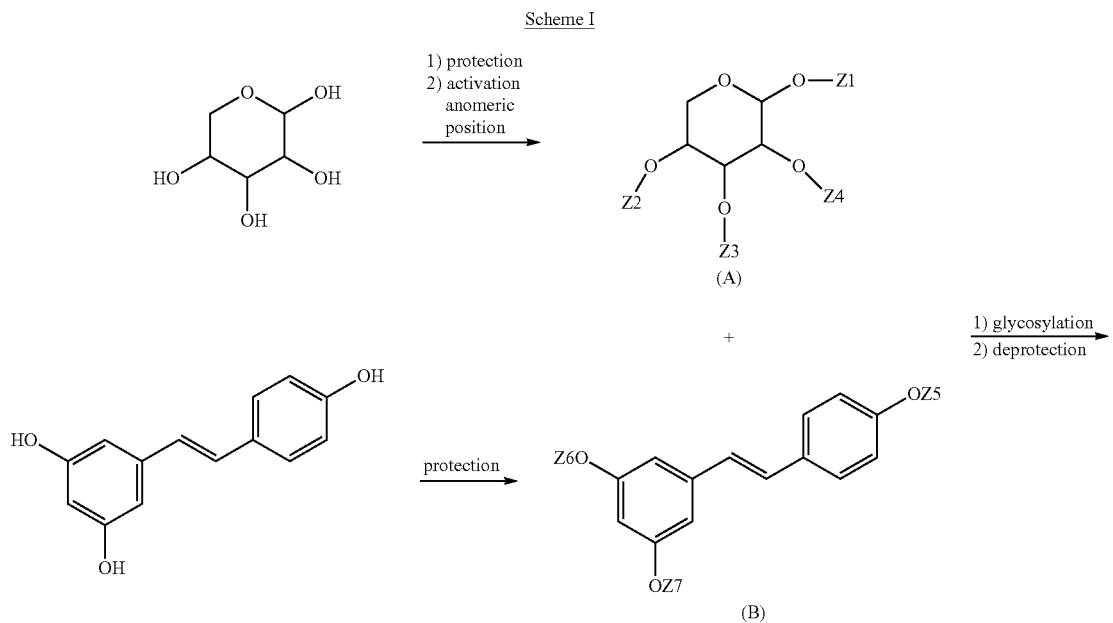

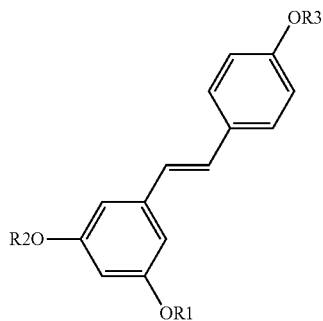

The compounds of the invention may be prepared according to the scheme I involving methods that are known and described for those skilled in the art. The resveratrol and also the xylose are orthogonally protected in (A) and (B) by methods known to those skilled in the art that are described in the book "Protecting Groups in Organic Synthesis" Greene, Wuts, Wiley Interscience, being understood that at least one of the groups Z5, Z6 and Z7 of (B) denotes a hydrogen atom. If the compound (B) bears several protective groups, the latter are preferably identical to one another.

The protective groups Z2, Z3 and Z4 are preferably identical to one another, it being understood that the protective groups borne by the compound (A) are different in nature to the protective groups borne by the compounds (B). Once protected, the compounds (A) and (B) are subjected to a chemical glycosylation reaction known to those skilled in the art, in particular in the book "Handbook of Chemical Glycosylation" A. V. Demchenko Wiley VCH. Once the new xyloside bond has formed, the hydroxyl groups are deprotected so as to give the compounds (I).

More specifically, the preparations of some compounds (I) are described in Zhongguo Yaowu Huaxue Zazhi (2010), 20(1), 19-24.

Alternatively, the compounds of formula (I) can be prepared according to schemes II or III below:

Scheme II

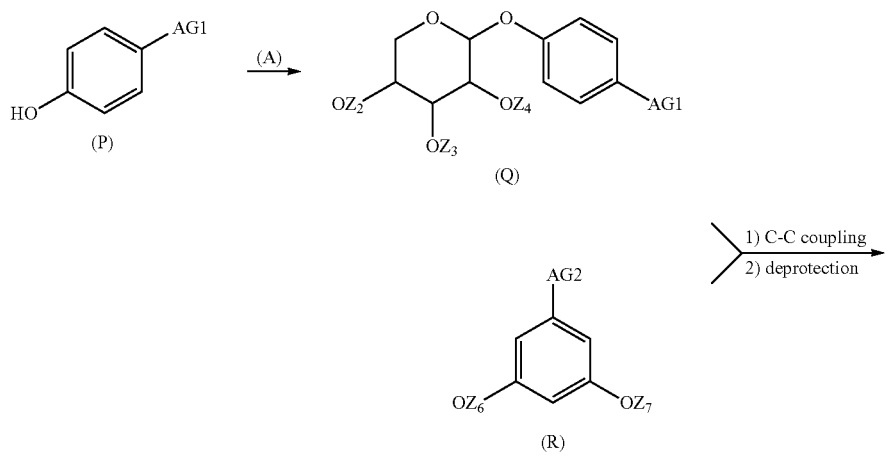

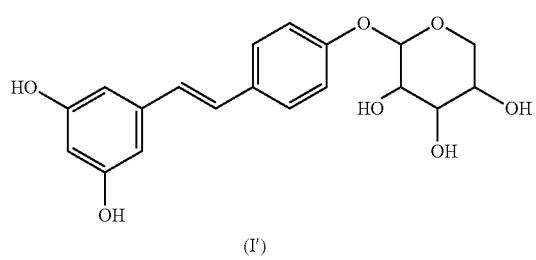

Scheme III

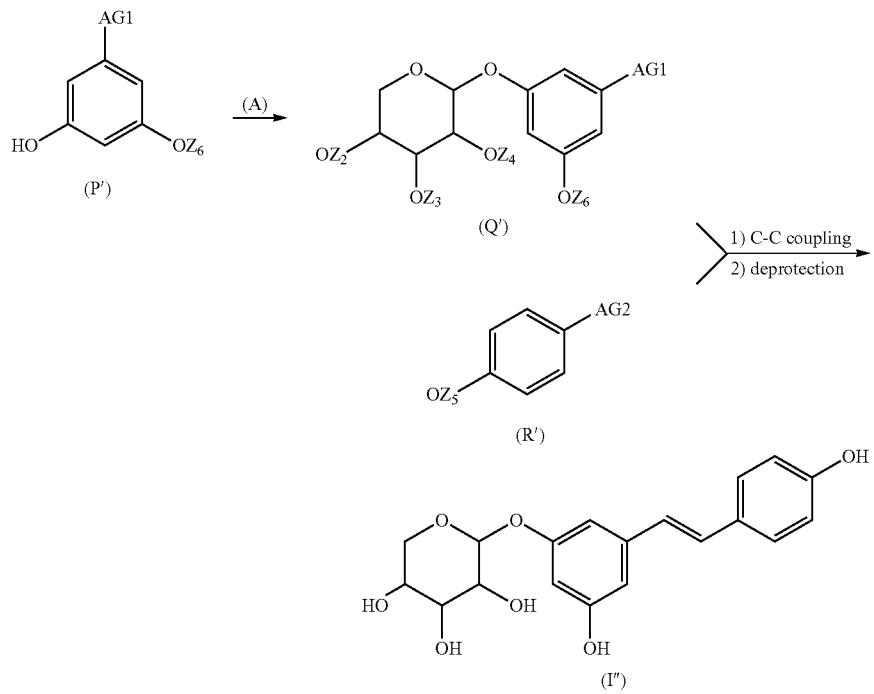

The compounds of the invention may be prepared according to the scheme II or III involving methods that are known and described for those skilled in the art. Compounds (I') which are O-glycosylated in position 4', or compounds (II') which are O-glycosylated in position 3, can be formed by a late stage C—C coupling step between compounds (Q) and (R), or compounds (Q') and (R'), respectively, before final deprotection. AG1 and AG2 are activated or functional groups compatible between them in order to be able to undergo a C—C coupling reaction generating a stilbenic double bond. As non-limitative examples, such C—C coupling reaction could be a Heck reaction between a halogen group (i.e. fluorine, chlorine, bromine or iodine) and a terminal olefin, a metathesis between two β-methyl-olefins (such as examples described in Green Chem. 2015, 17, 3756), a Wittig reaction between a methylene-halogen group and a methylene-phosphonium, or a Wittig-Horner reaction between a methylene-halogen group and a methylene-phosphonate (for example, as described in WO 2010046926, 2010, Preparation of novel stilbene analogs).

Precursors (Q) and (Q') can be generated from a glycosylation reaction of (P) and (P'), respectively.

Starting materials are orthogonally protected in (A), (R), (P') and (R') by methods known to those skilled in the art that are described in the book "Protecting Groups in Organic Synthesis" Greene, Wuts, Wiley Interscience.

Among the hydroxyl-radical-protecting groups $Z_i$ that can be used in the context of the invention, mention may for example be made of benzyl and tert-butyldimethylsilyl (TBS) groups.

The invention also relates to a composition, preferably a cosmetic composition, comprising, in a physiologically acceptable medium, at least one compound of formula (I) and also the salts thereof, the solvates thereof, and/or the isomers thereof.

The present invention also relates to a composition comprising, in a physiologically acceptable medium, at least one compound of formula (I) as described above. The composition is in particular a cosmetic composition.

The compound(s) of formula (I) may be present in the compositions in an amount which may be between 0.01% and 10% by weight, preferably between 0.1% and 5% by weight, in particular between 0.5% and 3% by weight, relative to the total weight of the composition.

The composition also comprises a physiologically acceptable medium, which will preferentially be a cosmetically acceptable medium, i.e. a medium which has no unpleasant odor, color or appearance, and which does not cause any tingling, tautness or discomfort unacceptable to the user. In particular, the composition is suitable for topical application to the skin.

The term "physiologically acceptable medium" is intended to mean a medium that is compatible with human keratin materials such as bodily or facial skin, the lips, mucous membranes, the eyelashes, the nails, the scalp and/or the hair.

In a particular embodiment the composition of the invention dose note comprise methanol and/or ethyl acetate.

The composition according to the invention may therefore comprise water and/or any of the cosmetic adjuvants normally used in the field of application envisaged. Mention may in particular be made of organic solvents, in particular $C_1$-$C_6$ alcohols and $C_2$-$C_{10}$ carboxylic acid esters; hydrocarbon-based oils, silicone oils, fluoro oils, waxes, pigments, fillers, dyes, surfactants, emulsifiers, cosmetic or dermatological active agents, film-forming polymers, hydrophilic or lipophilic gelling agents, thickeners, preservatives, fragrances, bactericides, odor absorbers and antioxidants.

These optional adjuvants may be present in the composition in a proportion of from 0.001% to 80% by weight and in particular from 0.1% to 40% by weight relative to the total weight of the composition.

Depending on their nature, these adjuvants may be introduced into the fatty phase or into the aqueous phase of the composition or into lipid vesicles. In any case, these adjuvants, and the proportions thereof, will be chosen by those skilled in the art such that the advantageous properties of the compounds according to the invention are not, or are not substantially, adversely affected by the envisaged addition.

As oils that can be used in the invention, mention may be made of mineral oils (liquid petroleum jelly), oils of plant origin (avocado oil, soybean oil), oils of animal origin (lanolin), synthetic oils (perhydrosqualene), silicone-based oils (cyclomethicone) and fluorinated oils (perfluoropolyethers). As fatty substances, use may also be made of fatty alcohols (cetyl alcohol), fatty acids, waxes (carnauba wax, ozokerite).

As hydrophilic thickeners or gelling agents, mention may be made of carboxyvinyl polymers (carbomer), acrylic copolymers such as acrylate/alkyl acrylate copolymers, polyacrylamides, polysaccharides, natural gums and clays, and, as lipophilic thickeners or gelling agents, mention may be made of modified clays such as bentones, metal salts of fatty acids and hydrophobic silica.

As cosmetic active agents, it will be advantageous to introduce into the composition according to the invention at least one compound chosen from: desquamating agents; calmatives, organic or mineral photoprotective agents, moisturizers; depigmenting agents; anti-glycation agents; NO-synthase inhibitors; agents, other than the compounds of the invention, for stimulating the synthesis of dermal or epidermal macromolecules and/or for preventing their degradation; agents, other than the compounds of the invention, for stimulating fibroblast and/or keratinocyte proliferation or for stimulating keratinocyte differentiation; dermo-decontracting agents; tensioning agents; anti-pollution agents and/or free-radical scavengers; agents acting on the microcirculation; agents acting on the energy metabolism of cells; and mixtures thereof.

This composition may be in any galenical form normally used in the cosmetics field, and especially in the form of an optionally gelled aqueous or aqueous-alcoholic solution, a dispersion, optionally a two-phase dispersion, of the lotion type, an emulsion obtained by dispersion of a fatty phase in an aqueous phase (O/W) or vice versa (W/O), or a triple (W/O/W or O/W/O) emulsion or a vesicular dispersion of ionic and/or nonionic type; aqueous or oily gels. These compositions are prepared according to the usual methods.

The composition may be more or less fluid and may have the appearance of a white or colored cream, an ointment, a milk, a lotion, a serum, a paste, a gel or a mousse. It may optionally be applied in the form of an aerosol. It may also be in solid form, in particular in stick form.

The composition according to the invention may constitute a skincare composition, in particular a cleansing, protection, treatment, or care cream for the face, for the hands, for the feet, for the major anatomical folds or for the body (for example, day creams, night creams, makeup-removing creams, foundation creams, antisun creams); a makeup-removing milk, a protective or care body milk or an antisun milk; or a lotion, a gel or foam for skincare, such as a cleansing lotion.

The composition according to the invention is advantageously an anti-aging, in particular care, composition intended for treating and/or combating, cosmetically, the external signs of the aging of keratin materials, preferably the external signs of skin aging; the composition is more particularly a care composition for mature skin.

The composition may also be a makeup composition, especially a foundation.

The invention also relates to the use of a cosmetic composition as previously defined comprising at least one compound of formula (I) as previously described, for cosmetically preventing and/or treating the signs of the aging of keratin materials, and in particular the signs on the skin.

The invention also relates to the use of a cosmetic composition as defined above comprising at least one compound of formula (I) as previously described, for preventing and/or cosmetically treating the signs of skin aging, in particular the signs on the skin which are chosen from wrinkled skin, skin exhibiting a detrimental modification of its viscoelastic or biomechanical properties, skin exhibiting a detrimental modification in the cohesion of its tissues, thinned skin, and skin exhibiting a detrimental modification of its surface appearance.

The invention also relates to the non-therapeutic cosmetic use of a composition as defined above comprising at least one compound of formula (I) as previously described, for improving the firmness of the skin and/or for improving the structure of the dermal-epidermal junction and/or for reinforcing the cohesion between the dermis and the epidermis.

The invention also relates to a process for non-therapeutic cosmetic treatment of keratin materials, in particular of the skin, comprising the application to said keratin materials of at least one compound of formula (I) as defined above, or of a cosmetic composition containing at least one compound of formula (I), as defined above.

The invention also relates to a process for cosmetic treatment of the skin, comprising the application to the skin of at least one compound of formula (I) as defined above, or of a cosmetic composition as defined above. This process has an advantageous application in the treatment of the skin, especially of mature skin and/or wrinkled skin, in particular of the face and/or of the neck and/or of the hands and more particularly of the face and/or the neck.

Novel Compounds

Some compounds of formula (I) as previously defined are novel and constitute another subject of the invention.

Thus, the compounds of formula (I) and also the salts thereof, the solvates thereof, and/or the isomers thereof as previously defined are novel with the exception of the compounds 1a and 2a as previously described.

| Compound | Structure | Chemical name |
|---|---|---|
| 1a | 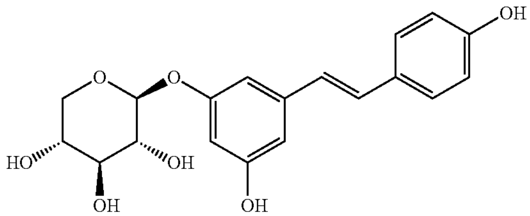 [SMILES: Oc1ccc(/C=C/c2cc(O)cc(O[C@@H]3OC[C@@H](O)[C@H](O)[C@H]3O)c2)cc1] | 3-hydroxy-5-[(E)-(4-hydroxyphenyl)ethenyl]phenyl β-D-xylopyranoside |
| 2a | 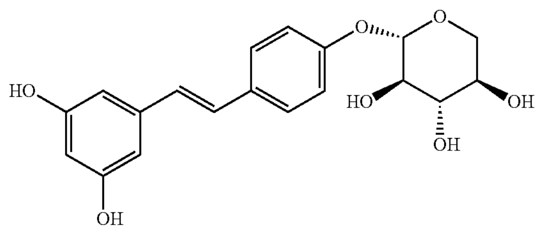 [SMILES: Oc1cc(O)cc(/C=C/c2ccc(O[C@@H]3OC[C@@H](O)[C@H](O)[C@H]3O)cc2)c1] | 4-[(E)-2-(3,5-dihydroxy-phenyl)ethenyl]phenyl β-D-xylopyranoside |

In particular, the compounds of formula (I) such that at least two of the radicals R1 and/or R2 and/or R3 denote a group of formula (II) as previously described are novel.

More particularly according to the invention these compounds of formula (I) are chosen from:

| Compound | Structure | Chemical name |
|---|---|---|
| 1b | 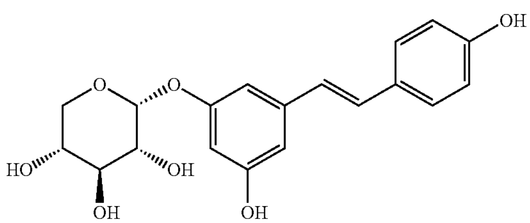 [SMILES: Oc1ccc(/C=C/c2cc(O)cc(O[C@H]3OC[C@@H](O)[C@H](O)[C@H]3O)c2)cc1] | 3-hydroxy-5-[(E)-2-(4-hydroxyphenyl)ethenyl]phenyl α-D-xylopyranoside |
| 2b | | 4-[(E)-2-(3,5-dihydroxy-phenyl)ethenyl]phenyl α-D-xylopyranoside | and also the salts thereof, the solvates thereof and/or the isomers thereof.

Among these compounds, mention may in particular be made of the compounds of formula (I) for which R1 and R3 denote a group of formula (II), and R2 denotes a hydrogen atom, and also the salts thereof, the solvates thereof, and/or the isomers thereof, it being possible for the anomeric-C bonds to be α or β anomeric and preferably β anomeric, it being possible for the isomers to be Z- or E-form isomers, in particular E-form isomers.

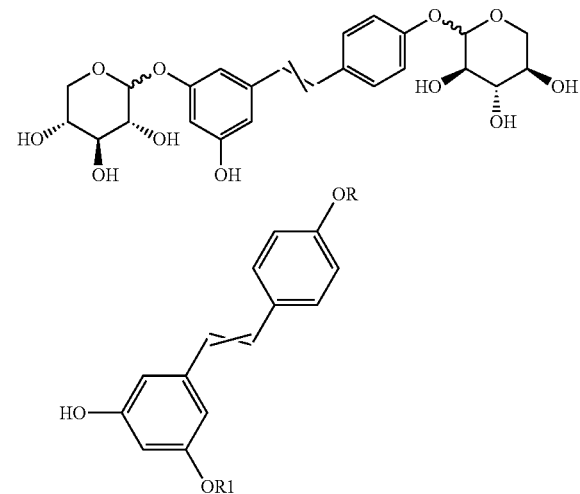

Mention may also be made of the novel compounds of formula (I) for which R2 and R3 denote a group of formula (II), and R1 denotes a hydrogen atom, and also the salts thereof, the solvates thereof, and/or the isomers thereof, it being possible for the anomeric-C bonds to be α or β anomeric and preferably β anomeric, it being possible for the isomers to be Z- or E-form isomers, in particular E-form isomers.

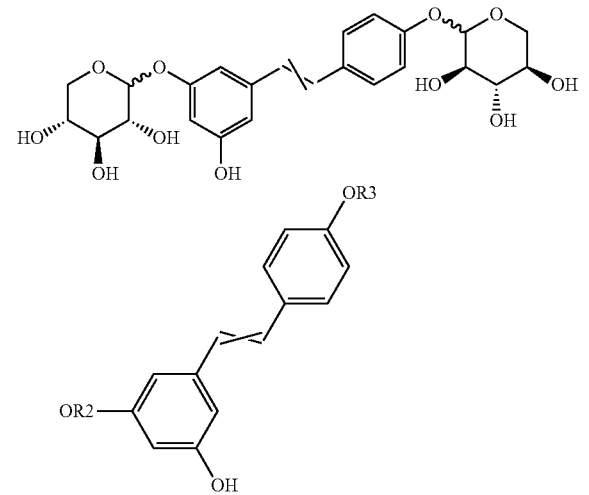

According to another variant of the invention, the novel compounds of formula (I) denote the compounds for which R1 denotes a group of formula (II) as previously described, R2 and R3 denoting a hydrogen atom, with the proviso that the isomers are Z isomers, it being possible for the anomeric-C bond to be α or β anomeric and preferably β anomeric.

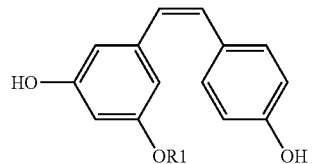

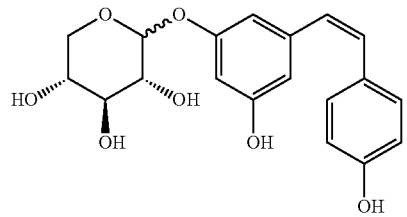

According to another variant of the invention, the novel compounds of formula (I) denote the compounds for which R3 denotes a group of formula (II) as previously described, R1 and R2 denoting a hydrogen atom, with the proviso that the isomers are Z isomers, it being possible for the anomeric-C bond to be α or β anomeric and preferably β anomeric.

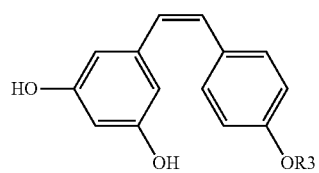

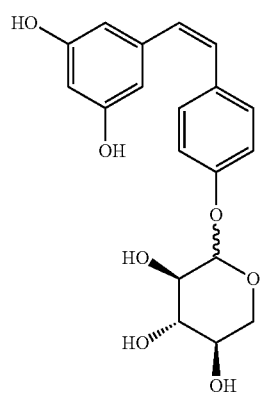

According to a another variant of the invention, the novel compounds of formula (I) denote the compounds for which R1 denotes a group of formula (II) as previously described, R2 and R3 denoting a hydrogen atom, with the proviso that the anomeric-C bond is α anomeric, the isomers being Z or E isomers and preferably E isomers.

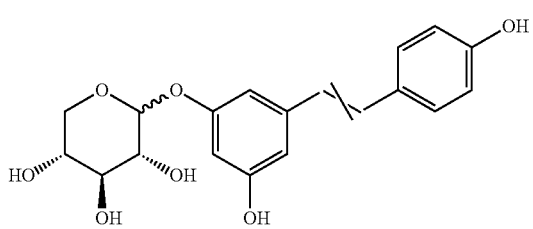
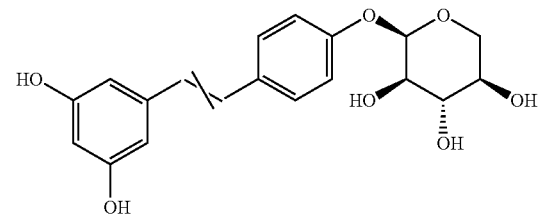

According to another variant of the invention, the novel compounds of formula (I) denote the compounds for which R3 denotes a group of formula (II) as previously described, R1 and R2 denoting a hydrogen atom, with the proviso that the anomeric-C bond is α anomeric, the isomers being Z or E isomers and preferably E isomers.

The invention also relates to the compositions, in particular cosmetic compositions, containing at least one novel compound as described above.

The invention is illustrated in greater detail by the following non-limiting examples.

EXAMPLE 1: SYNTHESIS OF THE COMPOUND 1A CAS: 195989-55-0

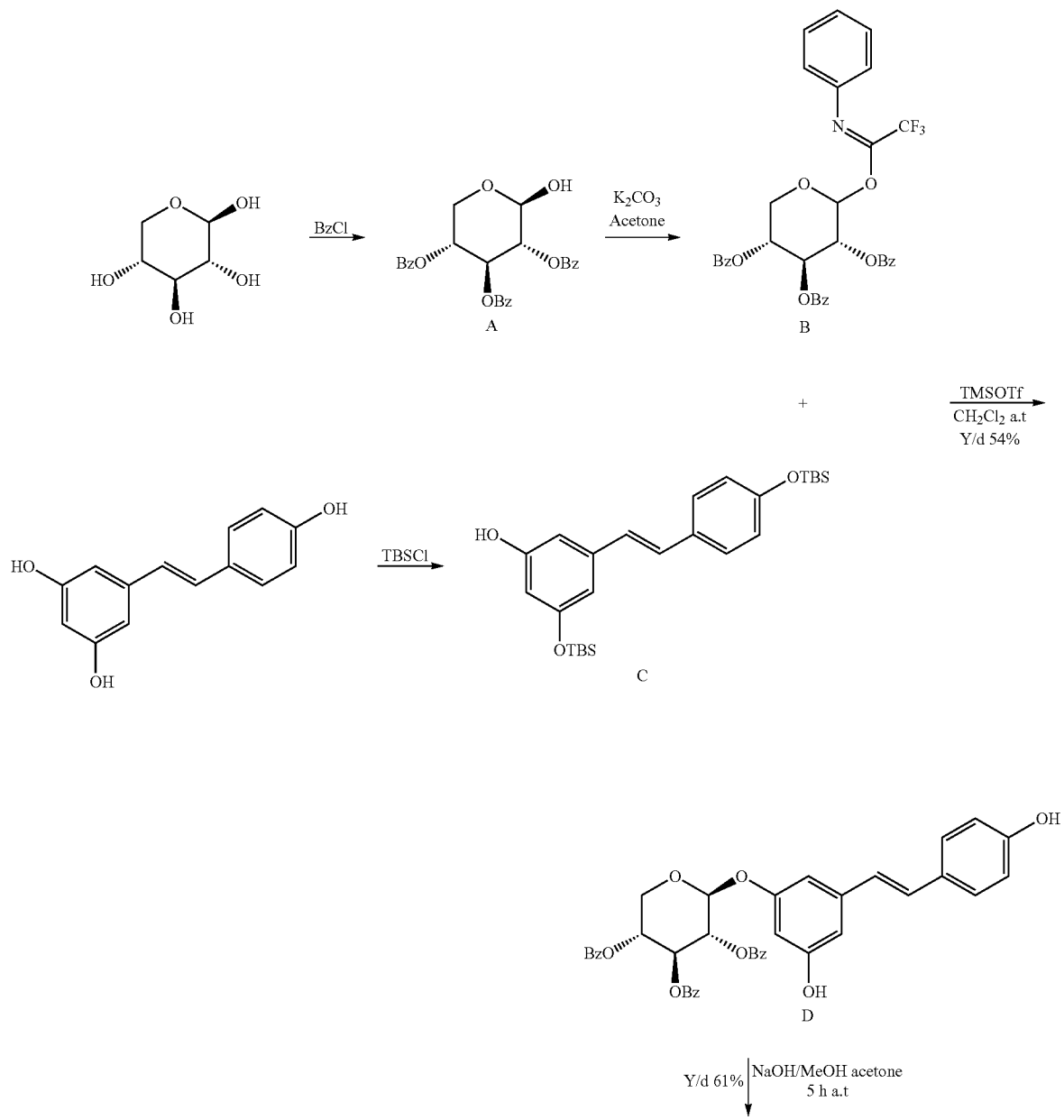

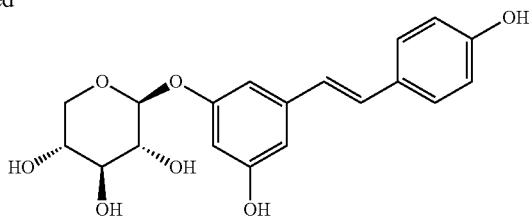

Compound 1a

The syntheses of the intermediates A and C are known to those skilled in the art and the synthesis is described in Zhongguo Yaowu Huaxue Zazhi (2010), 20(1), 19-24.

Synthesis of Compound B

Potassium carbonate (0.3 g 2.16 mmol) is added to a solution of compound A (0.5 g 1.08 mmol) and of trifluoro-N-phenylacetimidoyl chloride (CAS 61881-19-4) in 10 ml of acetone. The reaction mixture is stirred at ambient temperature for 1 h, then the heterogeneous mixture is subsequently filtered on diatomite and the filtrate is concentrated under vacuum. The residue is used without purification in the next step.

Synthesis of Compound D

Trimethylsilyltriflate (TMSOTf 5.4 mg 0.025 mmol) is added dropwise to a solution of crude compound B (0.21 g 0.34 mmol) and of compound C (0.15 g 0.24 mmol) in dichloromethane, and the reaction mixture is stirred at ambient temperature for 1 hour. The mixture is then concentrated under vacuum and the residue is purified on a silica chromatography column (eluent 8/1 petroleum ether/ethyl acetate) to give 0.12 g of compound D in the form of a white foam (54% yield).

Synthesis of the Compound 1a 3 ml of 2 M sodium hydroxide are added to a solution of compound D (0.12 g 0.13 mmol) in 6 ml of methanol/acetone (1/1 v/v). The reaction medium is stirred at ambient temperature for 5 h, then concentrated under vacuum and purified by MPLC preparative chromatography to give 30 mg of the compound 1a in the form of a white foam (62% yield).

The $^1$H NMR and mass spectra are in accordance with the structure of the expected product.

EXAMPLE 2: SYNTHESIS OF THE COMPOUND 2A CAS: 1245637-91-5

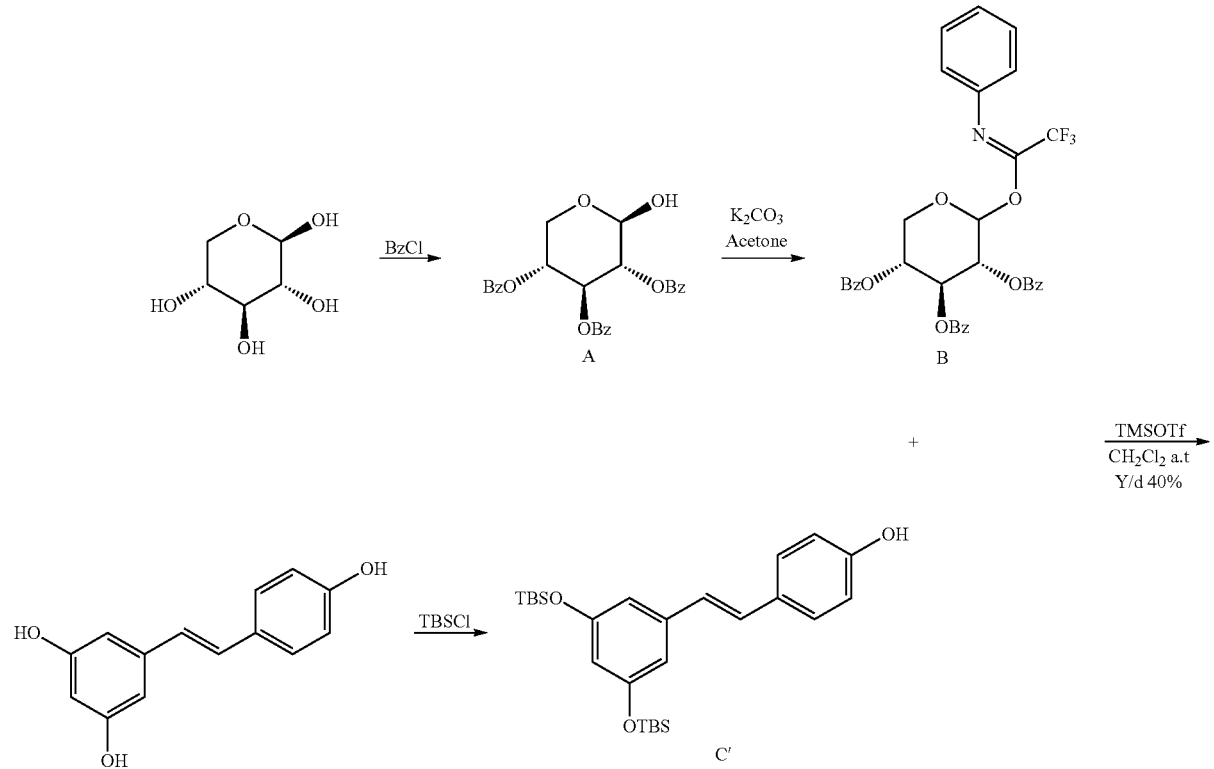

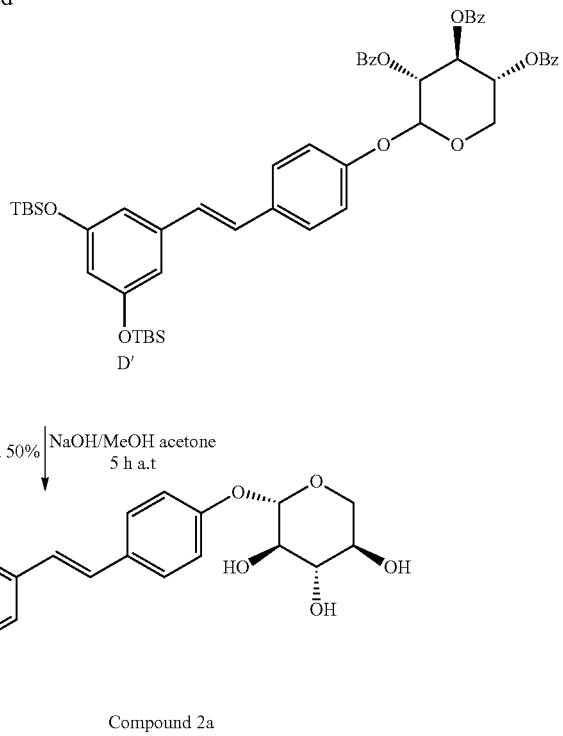

Compound 2a

Synthesis of Compound D'

Trimethylsilyltriflate (TMSOTf 5.4 mg 0.025 mmol) is added dropwise to a solution of crude compound B (0.21 g 0.34 mmol) and of compound C' (0.2 g 0.24 mmol) in dichloromethane, and the reaction mixture is stirred at ambient temperature for 1 hour. The mixture is then concentrated under vacuum and the residue is purified on a silica chromatography column (eluent 8/1 petroleum ether/ethyl acetate) to give 0.10 g of compound D' in the form of a white powder.

The syntheses of the intermediates A and C' are known to those skilled in the art and the synthesis is described in Zhongguo Yaowu Huaxue Zazhi (2010), 20(1), 19-24.

Synthesis of the Compound 2a 3 ml of 2 M sodium hydroxide are added to a solution of compound D' (0.10 g 0.10 mmol) in 6 ml of methanol/acetone (1/1 v/v). The reaction medium is stirred at ambient temperature for 5 h, then concentrated under vacuum and purified by preparative chromatography to give 25 mg of the compound 2a in the form of a white foam (53% yield).

The $^1$H NMR and mass spectra are in accordance with the structure of the expected product.

EXAMPLE 3: SYNTHESIS OF THE COMPOUND 2B (NOVEL COMPOUND)

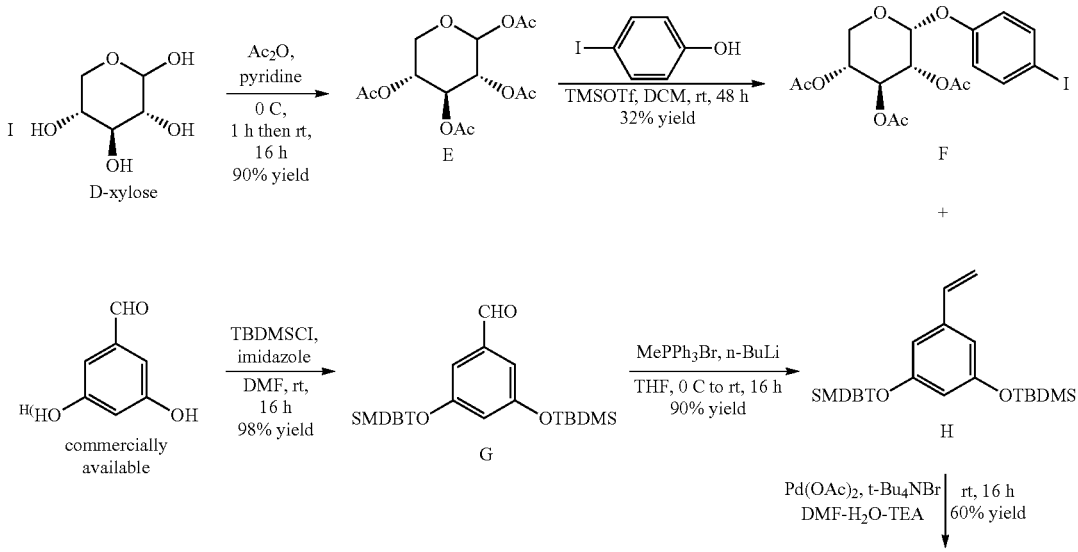

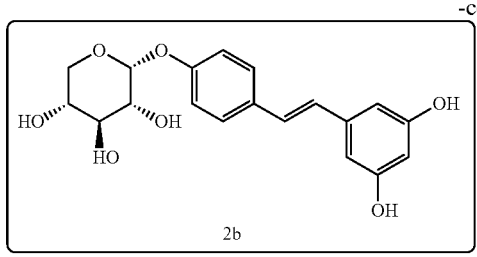

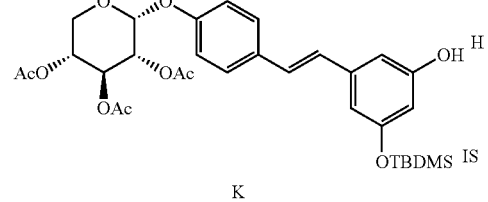

Synthesis of Compound E

To a stirred solution of D-xylose (7 g, 46.7 mmol) in 45 ml of pyridine at 0 C was added acetic anhydride (26 g, 255 mmol). The resulting mixture was stirred at rt for 16 h. After the solvent was removed, water and ethyl acetate were added. The organic layer was collected and washed with diluted HCl, aq. NaHCO3, and brine in sequence. Then, the extracts were dried over anhydrous Na2SO4, filtered, and evaporated in vacuo to give the compound E as a colorless oil. Yield: 14.7 g (99%)

Synthesis of Compound F

To a stirred solution of compound E (14.7 g, 46.3 mmol) and 4-iodophenol (11.2 g, 50.9 mmol) in 100 ml of dry dichloromethane was added 5 g of 4A molecular sieves under nitrogen. After the mixture was cooled to 0 C, TMSOTf (1 g, 4.6 mmol) was added via syringe. The reaction was stirred at rt for 24 h. Then, the mixture was cooled again to 0 C and another batch of TMSOTf (1 g, 4.6 mmol) was added via syringe. The reaction was continued to stir at rt for another 24 h and then quenched with aq. NaHCO3 solution. The organic layer was collected, dried over anhydrous Na2SO4, filtered, and evaporated in vacuo. The resulting residue was subjected to silica gel chromatography (petroleum ether/ethyl acetate=5/1) to give the compound F as a pale yellow solid. Yield: 7.19 g (32%)

Synthesis of Compound G

To a stirred solution of 3,5-dihydroxybenzaldehyde (5 g, 36.2 mmol) and imidazole (7.4 g, 108.7 mmol) in 30 ml of dry DMF at 0 C was added dropwise TBDMSCl (16.4 g, 108.7 mmol) under nitrogen. After the addition was complete, the mixture was stirred at 0 C for 1 h and then warmed to rt for another 16 h. The reaction was quenched with water and the mixture was extracted with ethyl acetate three times. The combined organic extracts were washed with water twice, aq. NaHCO3 once, and brine once. The organic phase was dried over anhydrous Na2SO4, filtered, and evaporated in vacuo. The resulting residue was subjected to silica gel chromatography (petroleum ether/ethyl acetate=100/1 to 20/1) to give the compound G as a colorless oil. Yield: 13.1 g (98%)

Synthesis of Compound H

To a stirred suspension of MePPh3Br (15.2 g, 42.6 mmol) in 100 ml of dry THF at 0 C was added dropwise 17 ml of 2.5 M n-BuLi-hexane solution under nitrogen. After the addition was complete, the mixture was stirred at 0 C for 1 h. Then, a solution of compound G (13 g, 35.5 mmol) in 20 ml of dry THF was added slowly to the above-mentioned mixture. The reaction was stirred at rt for 16 h and quenched with water. The organic layer was extracted with ethyl acetate twice. The combined organic extracts were dried over anhydrous Na2SO4, filtered, and evaporated in vacuo. The resulting residue was subjected to silica gel chromatography by using petroleum ether as an eluent to give the compound H as a colorless oil. Yield: 11.6 g (90%)

Synthesis of Compound K

To a stirred solution of compound F (7.19 g, 15.0 mmol) and compound H (6.57 g, 18.1 mmol) in 135 ml of DMF and 15 ml of water were added Pd(OAc)2 (1 g, 4.5 mmol), t-Bu4NBr (9.7 g, 30.0 mmol), and triethylamine (15 ml) under nitrogen. The reaction mixture was stirred at rt for 16 h. After filtration, the filtrate was diluted with water and then extracted with ethyl acetate twice. The combined organic extracts were washed with water three times and brine once, dried over anhydrous Na2SO4, filtered, and evaporated in vacuo. The resulting residue was subjected to silica gel chromatography (petroleum ether/ethyl acetate=3/1) to give the compound K as a yellow solid. Yield: 5.38 g (60%)

Synthesis of 2b

To a stirred methanol (100 ml) was added a grain of sodium (0.825 g, 36 mmol). After the sodium disappeared completely, a solution of compound K (5.38 g, 8.97 mmol) in 10 ml of dichloromethane was added. The mixture was stirred at rt for 16 h and then adjusted to pH~4 by addition of Amberlite IR-120(H) ion exchange resin. After filtration, the filtrate was evaporated to dryness. The resulting residue was subjected to silica gel chromatography (dichloromethane/methanol=10/1) to give the desired target 2b as a white solid. Yield: 1 g (31%)

The $^1$H NMR and mass spectra are in accordance with the structure of the expected product.

EXAMPLE 4: SYNTHESIS OF THE COMPOUND 1B (NOVEL COMPOUND)

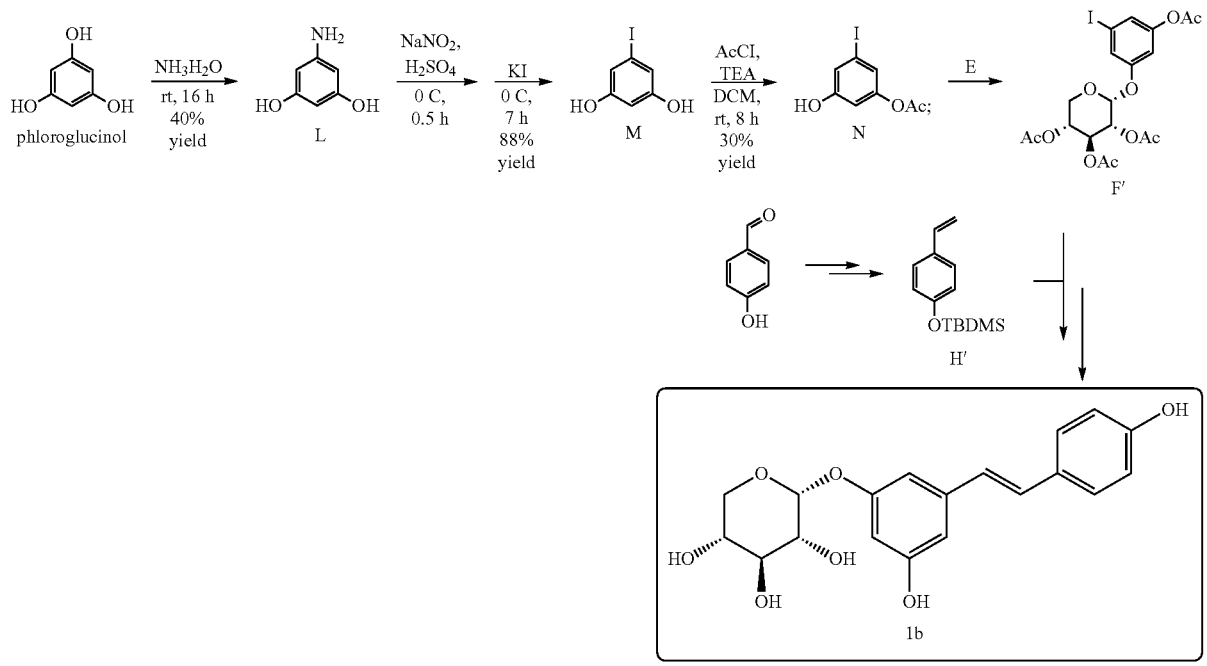

In the same manner than compound 2b, we could obtain compound 1b from coupling between F' and H'. H' could be prepared in the same way than H, starting from 4-hydroxy-benzaldehyde. F' could be prepared from coupling between N and E in the same process than F. N is synthesized in 3 steps starting from phloroglucinol. Phloroglucinol is treated with ammonia aqueous solution to give compound L. Then, diazotization of compound L with sodium nitrite followed by iodization with KI is carried out. After work-up, the desired compound M is isolated in 88% yield. Then, treatment of M with 1 equiv. of acetyl chloride gives compound N.

EXAMPLE 5: STUDY OF THE EFFECT OF COMPOUNDS ACCORDING TO THE INVENTION ON TOTAL AND SULFATED GLYCOSAMINOGLYCAN SYNTHESIS ON FIBROBLASTS AND ON KERATINOCYTES

The effects of the compounds on the neosynthesis of total and sulfated glycosaminoglycans (GAGs) were studied on two cell models, normal human epidermal keratinocytes (NHEKs) and normal human dermal fibroblasts (NHDFs). The effects of these compounds were evaluated by measuring:
- the incorporation of [3H]-glucosamine into the total GAGs neosynthesized by NHEKs and by NHDFs,
- the incorporation of [35S]-sulfate into the sulfated GAGs neosynthesized by NHEKs and by NHDFs.

The keratinocytes were seeded into wells and cultured in culture medium for 24 hours. The medium was then replaced with culture medium containing or not containing (control) the compounds to be tested or the reference (4-nitrophenyl β-D-xylopyranoside at 300 μM), then the cells were incubated for 72 hours with the addition of the [3H]-glucosamine radioactive label (total GAGs) or of the [35S]-sulfate radioactive label (sulfated GAGs) for the final 24 hours of incubation.

The fibroblasts were seeded into wells and cultured in culture medium for 24 hours. The medium was then replaced with culture medium containing or not containing (control) the compounds to be tested or the reference (TGF-β at 10 ng/ml), then the cells were incubated for 72 hours with the addition of the [35S]-sulfate radioactive label (sulfated GAGs) or of the [3H]-glucosamine radioactive label (total GAGs) for the final 24 hours of incubation.

At the end of the incubation, the glycosaminoglycans were extracted from the cells with a chaotropic buffer. The GAGs were then purified by ion exchange chromatography: adsorption of the anionic molecules on Q-Sepharose beads and desorption of the molecules of low or medium anionic nature, with a suitable solution.

The radioactivity incorporated into the molecules left on the support (GAGs, predominantly) was measured by liquid scintillation.

All the experimental conditions were performed in n=3.

The radioactivity incorporated into the molecules left on the support (GAGs, predominantly) was measured by liquid scintillation.

The inter-group comparisons were performed using Student's non-paired two-sided t-test. The statistical analyses can be interpreted if n≥5; however, for n<5, the data calculated are provided only by way of indication.

Standard error of the mean:

$$sem = \text{standard deviation (Sd)}/\sqrt{n}$$

The standard error of the mean (sem) represents the deviation of the sample mean relative to the true population mean. The sem is calculated by dividing the Sd by the square root of the sample size.

Cpm: counts per minute
Sd: standard deviation

TABLE 1

Effect of the compounds on the synthesis of total glycoaminoglycans by NHEKs (campaign 1)

| Comounds tested | Concentration | [$^3$H]-glucosamine (cpm) | Mean (cpm) | sem (cpm) | % Control | sem (%) | p$^{(1)}$ |
|---|---|---|---|---|---|---|---|
| Control | — | 13641 | 12928 | 474 | 100 | 4 | — |
| | | 12030 | | | | | |
| | | 13112 | | | | | |
| 4-Nitrophenyl β-D-xylopyranoside | 300 μM | 26835 | 26611 | 117 | 206 | 1 | *** |
| | | 26438 | | | | | |
| | | 26560 | | | | | |
| Compound 1a | 10 μM | 14440 | 15165 | 413 | 117 | 3 | * |
| | | 15184 | | | | | |
| | | 15871 | | | | | |
| | 100 μM | 30079 | 30380 | 811 | 235 | 6 | *** |
| | | 29149 | | | | | |
| | | 31911 | | | | | |
| Resveratrol | 10 μM | 7566 | 8328 | 393 | 64 | 3 | ** |
| | | 8537 | | | | | |
| | | 8880 | | | | | |
| | 100 μM | 1509 | 1743 | 132 | 13 | 1 | *** |
| | | 1754 | | | | | |
| | | 1967 | | | | | |
| Polydatin (resveratrol 4 glucoside) | 10 μM | 13405 | 13202 | 114 | 102 | 1 | ns |
| | | 13192 | | | | | |
| | | 13010 | | | | | |
| | 100 μM | 12222 | 11660 | 291 | 90 | 2 | ns |
| | | 11510 | | | | | |
| | | 11248 | | | | | |

Threshold for statistical significance
ns: >0.05, Not significant
*: 0.01 to 0.05, Significant
**: 0.001 to 0.01, Very significant
***: <0.001, Extremely significant Threshold for Statistical Significance
ns: >0.05, Not significant
*: 0.01 to 0.05, Significant
**: 0.001 to 0.01, Very significant
***: <0.001, Extremely significant

TABLE 2

Effect of the compounds on the synthesis of sulfated glycosaminoglycans by NHEKs (campaign 1)

| Compounds tested | Concentration | [$^{35}$S]-Sulfate (cpm) | Mean (cpm) | sem (cpm) | % Control | sem (%) | p$^{(1)}$ |
|---|---|---|---|---|---|---|---|
| Control | — | 6093 | 6784 | 355 | 100 | 5 | — |
| | | 6988 | | | | | |
| | | 7271 | | | | | |
| 4-Nitrophenyl β-D-xylopyranoside | 300 μM | 60267 | 62566 | 1164 | 922 | 17 | *** |
| | | 63396 | | | | | |
| | | 64036 | | | | | |
| Compound 1a | 10 μM | 9304 | 9319 | 113 | 137 | 2 | ** |
| | | 9522 | | | | | |
| | | 9131 | | | | | |
| | 100 μM | 53801 | 56923 | 1861 | 839 | 27 | *** |
| | | 56728 | | | | | |
| | | 60239 | | | | | |
| Resveratrol | 10 μM | 5238 | 5254 | 141 | 77 | 2 | * |
| | | 5506 | | | | | |
| | | 5018 | | | | | |
| | 100 μM | 1836 | 1802 | 39 | 27 | 1 | *** |
| | | 1725 | | | | | |
| | | 1845 | | | | | |

TABLE 2-continued

Effect of the compounds on the synthesis of sulfated glycosaminoglycans by NHEKs (campaign 1)

| Compounds tested | Concentration | [$^{35}$S]-Sulfate (cpm) | Mean (cpm) | sem (cpm) | % Control | sem (%) | p$^{(1)}$ |
|---|---|---|---|---|---|---|---|
| Polydatin | 10 μM | 6316 | 6760 | 246 | 100 | 4 | ns |
|  |  | 6800 |  |  |  |  |  |
|  |  | 7164 |  |  |  |  |  |
|  | 100 μM | 7007 | 8043 | 530 | 119 | 8 | ns |
|  |  | 8365 |  |  |  |  |  |
|  |  | 8756 |  |  |  |  |  |

In another series of assays, compound 2a was tested as well.

TABLE 3

Effect of the compounds on the synthesis of total and sulfated glycosaminoglycans by NHEKs (campaign 2)

| Compound tested | Concentration | [$^3$H]-glucosamine (cpm) | Mean (cpm) | esm (cpm) | % Control | esm (%) | p$^{(1)}$ |
|---|---|---|---|---|---|---|---|
| Control | — | 7024 | 8513 | 747 | 100 | 9 | — |
|  |  | 9373 |  |  |  |  |  |
|  |  | 9142 |  |  |  |  |  |
| 4-Nitrophenyl β-D-xylopyranoside | 300 μM | 22239 | 20694 | 975 | 243 | 11 | *** |
|  |  | 20953 |  |  |  |  |  |
|  |  | 18891 |  |  |  |  |  |
| Resveratrol | 1 μM | 10734 | 9628 | 774 | 113 | 9 | ns |
|  |  | 10012 |  |  |  |  |  |
|  |  | 8137 |  |  |  |  |  |
|  | 10 μM | 6772 | 7347 | 404 | 86 | 5 | ns |
|  |  | 7143 |  |  |  |  |  |
|  |  | 8126 |  |  |  |  |  |
| Compound 1a | 10 μM | 10145 | 11405 | 638 | 134 | 7 | * |
|  |  | 11857 |  |  |  |  |  |
|  |  | 12213 |  |  |  |  |  |
|  | 100 μM | 16745 | 16980 | 324 | 199 | 4 | *** |
|  |  | 16574 |  |  |  |  |  |
|  |  | 17621 |  |  |  |  |  |
| Compound 2a | 1 μM | 9472 | 10215 | 455 | 120 | 5 | ns |
|  |  | 10133 |  |  |  |  |  |
|  |  | 11041 |  |  |  |  |  |
|  | 10 μM | 11913 | 12844 | 680 | 151 | 8 | * |
|  |  | 12452 |  |  |  |  |  |
|  |  | 14167 |  |  |  |  |  |

| Compound tested | Concentration | [$^{35}$S]-Sulfate (cpm) | Mean (cpm) | esm (cpm) | % Control | esm (%) | p$^{(1)}$ |
|---|---|---|---|---|---|---|---|
| Control | — | 5021 | 5309 | 195 | 100 | 4 | — |
|  |  | 5680 |  |  |  |  |  |
|  |  | 5227 |  |  |  |  |  |
| 4-Nitrophenyl B-D-xylopyranoside | 300 μM | 54440 | 54615 | 1078 | 1029 | 20 | *** |
|  |  | 52841 |  |  |  |  |  |
|  |  | 56564 |  |  |  |  |  |
| Resveratrol | 1 μM | 6885 | 6530 | 322 | 123 | 6 | * |
|  |  | 6817 |  |  |  |  |  |
|  |  | 5888 |  |  |  |  |  |
|  | 10 μM | 5137 | 4973 | 97 | 94 | 2 | ns |
|  |  | 4981 |  |  |  |  |  |
|  |  | 4802 |  |  |  |  |  |
| Compound 1a | 10 μM | 10206 | 11501 | 684 | 217 | 13 | *** |
|  |  | 12532 |  |  |  |  |  |
|  |  | 11765 |  |  |  |  |  |
|  | 100 μM | 46568 | 51673 | 2553 | 973 | 48 | *** |
|  |  | 54125 |  |  |  |  |  |
|  |  | 54327 |  |  |  |  |  |

TABLE 3-continued

Effect of the compounds on the synthesis of total and sulfated glycosaminoglycans by NHEKs (campaign 2)

| Compound 2a | 1 μM | 5974 | 6073 | 149 | 114 | 3 | * |
| | | 6365 | | | | | |
| | | 5879 | | | | | |
| | 10 μM | 11209 | 12748 | 777 | 240 | 15 | *** |
| | | 13332 | | | | | |
| | | 13703 | | | | | |

The treatment of the normal human epidermal keratinocytes (NHEKs) with the 4-nitrophenyl β-D-xylopyranoside reference, tested at 300 μM, stimulated the neosynthesis of the total GAGs and that of the sulfated GAGs (respectively 206%/243% and 922%/1029% of the control, tables 1, 2 and 3).

The polydatin compound, tested at 10 and 100 μM, did not modulate the neosynthesis of the sulfated and total GAGs by the NHEKs (tables 1 and 2).

The resveratrol compound, tested at 10 and 100 μM, inhibited, in a concentration-dependent manner, the neosynthesis of the total and sulfated GAGs by the NHEKs (tables 1 and 2).

Surprisingly, the compound 1a tested at 10 and 100 μM, stimulated, in a concentration-dependent manner, the neosynthesis of the total GAGs (117% and 235%, respectively, table 1; 134% and 199%, respectively, table 3) and strongly stimulated in a concentration-dependent manner the neosynthesis of the sulfated GAGs by the NHEKs (137% and 839%, respectively, table 2; 217% and 973%, respectively, table 3).

In the same manner, surprisingly the compound 2a tested at 1 and 10 μM, stimulated in a concentration-dependent manner, the neosynthesis of the total GAGs as well as the neosynthesis of the sulfated GAGs by the NHEKs (table 3).

TABLE 4

Effect of the compounds on the synthesis of sulfated glycosaminoglycans by NHDFs (campaign 1)

| Compound tested | Concentration | [$^{35}$S]-Sulfate (cpm) | Mean (cpm) | sem (cpm) | % Control | sem (%) | $p^{(1)}$ |
|---|---|---|---|---|---|---|---|
| Control | — | 1678 | 1647 | 16 | 100 | 1 | — |
| | | 1639 | | | | | |
| | | 1624 | | | | | |
| TGF-β | 10 ng/ml | 3397 | 3433 | 30 | 208 | 2 | *** |
| | | 3492 | | | | | |
| | | 3411 | | | | | |
| Compound 1a | 10 μM | 3286 | 3472 | 93 | 211 | 6 | *** |
| | | 3573 | | | | | |
| | | 3557 | | | | | |
| | 100 μM | 8753 | 8844 | 210 | 537 | 13 | *** |
| | | 8534 | | | | | |
| | | 9244 | | | | | |
| Resveratrol | 10 μM | 1506 | 1527 | 15 | 93 | 1 | ** |
| | | 1556 | | | | | |
| | | 1519 | | | | | |
| | 100 μM | 967 | 1019 | 26 | 62 | 2 | *** |
| | | 1045 | | | | | |
| | | 1046 | | | | | |
| Polydatin | 10 μM | 1523 | 1573 | 73 | 96 | 4 | ns |
| | | 1479 | | | | | |
| | | 1718 | | | | | |
| | 100 μM | 1290 | 1287 | 18 | 78 | 1 | *** |
| | | 1317 | | | | | |
| | | 1255 | | | | | |

In another series of assays, compound 2a was tested as well.

TABLE 5

Effect of the compounds on the synthesis of total and sulfated glycosaminoglycans by NHDFs (campaign 2)

| Compound tested | Concentration | [$^{3}$H]-glucosamine (cpm) | Mean (cpm) | esm (cpm) | % Control | esm (%) | $p^{(1)}$ |
|---|---|---|---|---|---|---|---|
| Control | — | 1515 | 1562 | 58 | 100 | 4 | — |
| | | 1493 | | | | | |
| | | 1677 | | | | | |

TABLE 5-continued

Effect of the compounds on the synthesis of total and sulfated glycosaminoglycans by NHDFs (campaign 2)

| | | | | | | | |
|---|---|---|---|---|---|---|---|
| TGF-β | 10 ng/ml | 5999<br>4173<br>5328 | 5167 | 533 | 331 | 34 | ** |
| Resveratrol | 10 μM | 1439<br>1533<br>1630 | 1534 | 55 | 98 | 4 | ns |
| | 100 μM | 1253<br>1360<br>1404 | 1339 | 45 | 86 | 3 | * |
| Compound 1a | 10 μM | 1622<br>1750<br>1680 | 1684 | 37 | 108 | 2 | ns |
| | 100 μM | 1422<br>1331<br>1470 | 1408 | 41 | 90 | 3 | ns |
| Compound 2a | 10 μM | 1758<br>1479<br>1636 | 1624 | 81 | 104 | 5 | ns |
| | 100 μM | 1958<br>1959<br>2003 | 1973 | 15 | 126 | 1 | ** |

| Compound tested | Concentration | [$^{35}$S]-Sulfate (cpm) | Mean (cpm) | esm (cpm) | % Control | esm (%) | p$^{(1)}$ |
|---|---|---|---|---|---|---|---|
| Control | — | 564<br>513<br>621 | 566 | 31 | 100 | 6 | — |
| TGF-β | 10 ng/ml | 1471<br>1482<br>1403 | 1452 | 25 | 257 | 4 | *** |
| Resveratrol | 10 μM | 613<br>513<br>586 | 571 | 30 | 101 | 5 | ns |
| | 100 μM | 355<br>283<br>276 | 305 | 25 | 54 | 4 | ** |
| Compound 1a | 10 μM | 1274<br>1307<br>1180 | 1254 | 38 | 221 | 7 | *** |
| | 100 μM | 2237<br>2369<br>2379 | 2328 | 46 | 411 | 8 | *** |
| Compound 2a | 10 μM | 765<br>835<br>786 | 795 | 21 | 141 | 4 | ** |
| | 100 μM | 2858<br>3230<br>2958 | 3015 | 111 | 533 | 20 | *** |

The treatment of the normal human dermal fibroblasts (NHDFs) with the TGF-β reference, tested at 10 ng/ml, stimulated the neosynthesis of total and sulfated GAGs (respectively 331% and 208%/257% of the control, tables 4 and 5).

The resveratrol and polydatin compounds, tested at 10 and 100 μM, overall inhibited the neosynthesis of the total and sulfated GAGs by the NHDFs in a concentration-dependent manner (tables 4 and 5).

Surprisingly, the compound 1a, tested at 10 and 100 μM, strongly stimulated, in a concentration-dependent manner, the neosynthesis of the sulfated GAGs by the NHDFs (211% and 537%, respectively, table 4; 221% and 411%, respectively, table 5).

In addition, surprisingly the compound 2a tested at 10 and 100 μM, stimulated in a concentration-dependent manner, the neosynthesis of the total GAGs (table 5), and strongly stimulated in a concentration-dependent manner, the neosynthesis of the sulfated GAGs by the NHDFs (141% and 533%, respectively, table 5).

The effect of compound 2a and compound 2b on the neosynthesis of total and sulfated glycosaminoglycans (GAGs) were studied on two cell models, normal human epidermal keratinocytes (NHEKs) and normal human dermal fibroblasts (NHDFs) is evaluated.

EXAMPLE 6

An anti-aging gel for the skin is prepared, comprising (% by weight):

| | |
|---|---|
| compound 1a of example 1 | 2% |
| hydroxypropylcellulose (Klucel H from Hercules) | 1% |
| antioxidant | qs |
| fragrance, preservative | qs |
| isopropanol | 40% |
| water | qs 100% |

A similar composition is prepared with the compound of example 2.

A similar composition is prepared with the compound of example 3 or with the compound of example 4.

The composition applied to the face makes it possible to reinforce the firmness of the skin and thus to soften the signs of skin aging.

The invention claimed is:

1. A process for reducing and/or treating the signs of the aging of keratin material, which comprises applying to the keratin material at least one compound of formula (I):

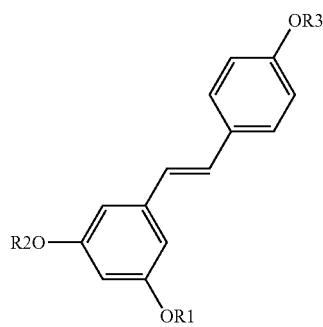

in which R1, R2 and R3 independently denote:
a group of formula (II), (II)

in which the asterisk "*" denotes the point of attachment of the radical to the rest of the compound, or
a hydrogen atom H,
wherein at least one of the radicals R1, R2, R3 denotes a group of formula (II);
the salts thereof, the solvates thereof, and/or the isomers thereof.

2. The process as claimed in claim 1, wherein:
R1 denotes a group of formula (II)

(II)

and
R2 and R3 each denote a hydrogen atom H.

3. The process as claimed in claim 1, wherein:
R2 denotes a group of formula (II)

(II)

and
R1 and R3 each denote a hydrogen atom H.

4. The process as claimed in claim 1, wherein the compound is chosen from the following compounds:

| Compound | Structure | Chemical name |
|---|---|---|
| 1 | 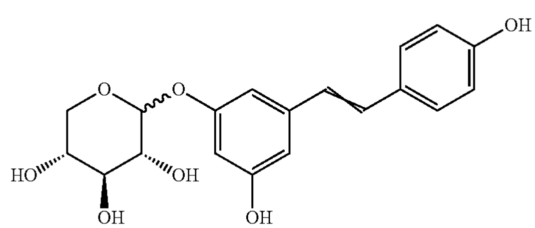 [SMILES: Oc1ccc(C=Cc2cc(O)cc(OC3OC[C@@H](O)[C@H](O)[C@H]3O)c2)cc1] | 3-hydroxy-5-[2-(4-hydroxyphenyl)ethenyl]phenyl xylopyranoside |
| 2 | | 4-[2-(3,5-dihydroxyphenyl)ethenyl]phenyl xylopyranoside | and the salts thereof, the solvates thereof and/or the isomers thereof.

5. The process as claimed in claim 1, wherein the compound is chosen from the following compounds:

| Compound | Structure | Chemical name |
|---|---|---|
| 1a | 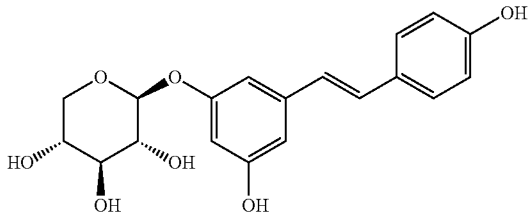 [SMILES: Oc1ccc(/C=C/c2cc(O)cc(O[C@@H]3OC[C@@H](O)[C@H](O)[C@H]3O)c2)cc1] | 3-hydroxy-5-[(E)-2-(4-hydroxyphenyl)ethenyl]phenyl β-D-xylopyranoside |
| 2a | 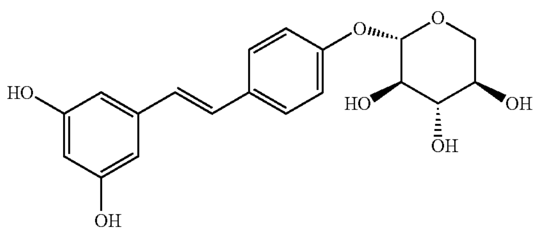 [SMILES: Oc1cc(O)cc(/C=C/c2ccc(O[C@@H]3OC[C@@H](O)[C@H](O)[C@H]3O)cc2)c1] | 4-[(E)-2-(3,5-dihydroxyphenyl)ethenyl]phenyl β-D-xylopyranoside |
| 1b | 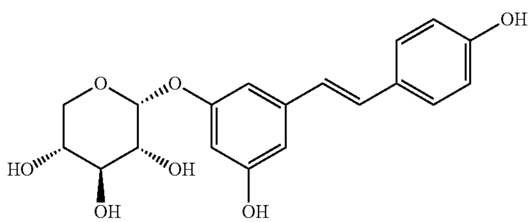 [SMILES: Oc1ccc(/C=C/c2cc(O)cc(O[C@H]3OC[C@@H](O)[C@H](O)[C@H]3O)c2)cc1] | 3-hydroxy-5-[(E)-2-(4-hydroxyphenyl)ethenyl]phenyl a-D-xylopyranoside |
| 2b | | 4-[(E)-2-(3,5-dihydroxyphenyl)ethenyl]phenyl a-D-xylopyranoside | and the salts thereof, the solvates thereof and/or the isomers thereof.

6. A process for the non-therapeutic cosmetic treatment of the skin, comprising the application to the skin of at least one compound of formula (I) as defined in claim 1 or of a composition comprising said at least one compound.

7. The process as claimed in claim 6, wherein the composition is applied to mature and/or wrinkled skin.

8. A process for the non-therapeutic treatment for improving the firmness of the skin, comprising applying to the skin at least one compound of formula (I) as defined in claim 1 or of a composition comprising said at least one compound.

9. A process for the non-therapeutic treatment of signs of photoinduced or hormonal aging of the skin, comprising applying to the skin at least one compound of formula (I) as defined in claim 1 or of a composition comprising said at least one compound.

* * * * *